US00PP25660P2

(12) United States Plant Patent
Lannes

(10) Patent No.: US PP25,660 P2
(45) Date of Patent: Jun. 30, 2015

(54) ***HIBISCUS* PLANT NAMED 'LANLAMPASAS'**

(50) Latin Name: *Hibiscus rosa-sinensis*
Varietal Denomination: Lanlampasas

(71) Applicant: Robert Lannes, Malause (FR)

(72) Inventor: Robert Lannes, Malause (FR)

( * ) Notice: Subject to any disclaimer, the term of this patent is extended or adjusted under 35 U.S.C. 154(b) by 184 days.

(21) Appl. No.: 13/987,551

(22) Filed: Aug. 6, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — June Hwu
(74) *Attorney, Agent, or Firm* — Penny J. Aguirre

(57) ABSTRACT

A new cultivar of *Hibiscus* named 'Lanlampasas', characterized by its very large flowers that have red centers and wide golden orange margins, its short leaf internode lengths, its very dark green foliage, its good self-branching, and its very vigorous growth habit.

2 Drawing Sheets

Botanical classification: *Hibiscus rosa-sinensis*.
Cultivar designation: 'Lanlampasas'.

BACKGROUND OF THE INVENTION

The present invention relates to a new and distinct cultivar of *Hibiscus* plant of hybrid origin, botanically known as *Hibiscus rosa-sinensis* 'Lanlampasas' and will be referred to hereafter by its cultivar name, 'Lanlampasas'. 'Lanlampasas' is a new cultivar of tropical *hibiscus* grown for use as a landscape and container plant.

The new cultivar was developed through an on-going breeding program conducted by the Inventor in Malause, France. The objectives of the breeding program are to develop new cultivars of *Hibiscus* that exhibit compact plant habits with self-branching and a well-balanced plant habit.

The Inventor made a cross in July of 2006 between 'Adele' (not patented) as the female parent and 'Soleil Ambre' (not patented) as the male parent. 'Lanlampasas' was selected as a single unique plant from the resulting seedlings in September of 2009.

Asexual propagation of the new cultivar was first accomplished by stem cuttings in Malause, France in September of 2009 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics 'Lanlampasas'. These attributes in combination distinguish 'Lanlampasas' as a new and distinct cultivar of *Hibiscus*.

1. 'Lanlampasas' exhibits very large flowers that have red centers and wide golden orange margins.
2. 'Lanlampasas' exhibits short leaf internode lengths.
3. 'Lanlampasas' exhibits very dark green foliage.
4. 'Lanlampasas' exhibits good self-branching.
5. 'Lanlampasas' exhibits a very vigorous growth habit.

Both the female parent of 'Lanlampasas', 'Adele', and the male parent, 'Soleil Ambre', differ from 'Lanlampasas' in having smaller flowers with very little red coloration and in having stems with less self-branching. In addition, 'Adele' has a less vigorous growth habit. 'Lanlampasas' can also be most closely compared to the cultivars 'Apollo' (U.S. Plant Pat. No. 23,072) and 'Madrid' (not patented). Both are similar to 'Lanlampasas' in having flowers that are orange in color with red centers. 'Apollo' differs from 'Lanlampasas' in having much smaller flowers with centers that are lighter red in color with pink stripes from the base to the margins of the petals and in having longer leaf internodes. 'Madrid' differs from 'Lanlampasas' in having smaller flowers with a very small red center (mostly orange) and in having a less vigorous growth habit.

BRIEF DESCRIPTION OF THE DRAWING

The accompanying colored photograph illustrates the overall appearance and distinct characteristics of the new *Hibiscus*. The photographs were taken of a six month-old plant of 'Lanlampasas' as grown in a one-gallon container in a greenhouse in Malause, France.

The photograph in FIG. 1 provides a side view of 'Lanlampasas' in bloom.

Figure 1:
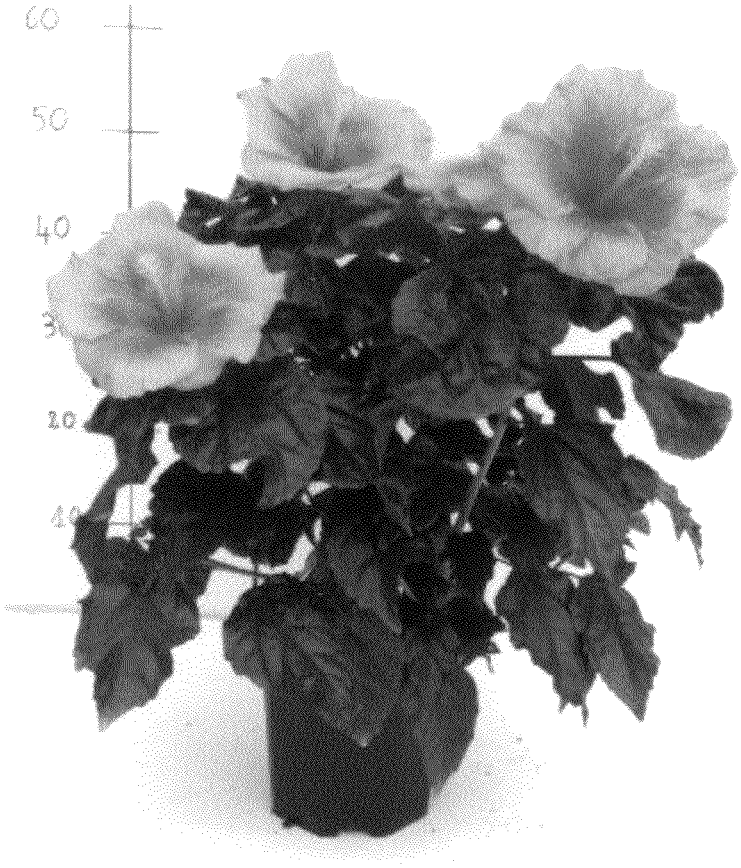
Figure 2:
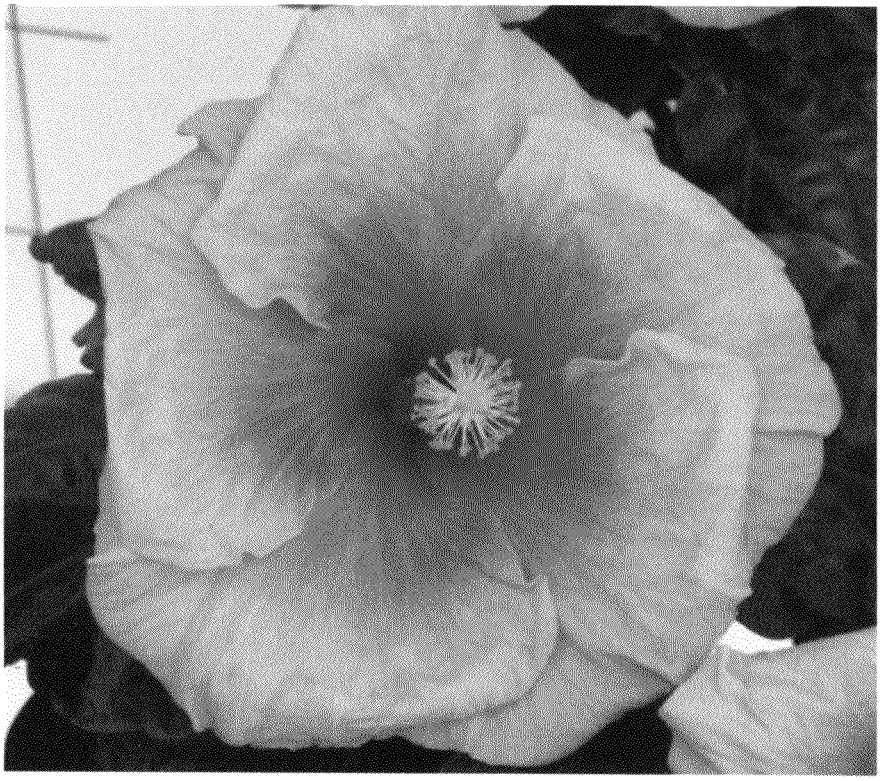

The photograph in FIG. 2 provides a close-up view of a flower of 'Lanlampasas'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 8 month-old plants of the new cultivar as grown in two-quart containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Continuously through summer in Grand Saline, Tex. and Malause, France.

*Plant type.*—Tropical evergreen shrub.

*Plant habit.*—Upright and slightly spreading, compact.

*Height and spread.*—Reaches 35 to 45 cm in height and 30 to 40 cm in spread.

*Hardiness.*—At least in U.S.D.A. Zones 9 to 11.

*Diseases.*—Not susceptible or resistance to diseases has been observed.

*Root description.*—Fibrous roots.

*Propagation.*—Stem cutting.

*Growth rate.*—Very vigorous.

Stem description:

*Shape.*—Slightly oval.

*Stem color.*—New growth; 143A with some spots of 177A and 156B.

*Stem size.*—Main stems; an average of 21 cm in length and 4 mm in width.

*Stem surface.*—New growth; glabrous, bark; finely striated.

*Stem aspect.*—Held upright to an average angle of 30° (0°=vertical).

*Stem strength.*—Strong.

*Branching.*—Self-branching, an average of 2 main stems in a 2-quart container.

*Internode.*—Average of 3 cm.

Foliage description:

*Leaf shape.*—Ovate.

*Leaf division.*—Simple.

*Leaf base.*—Rounded.

*Leaf apex.*—Acute.

*Leaf venation.*—Pinnate, 137C in color on upper and lower surface.

*Leaf margins.*—Serrate and wavy.

*Leaf attachment.*—Petiolate.

*Leaf arrangement.*—Whorled.

*Leaf orientation.*—Held sideways to slightly upward.

*Leaf aspect.*—Flat and slightly cupped inward.

*Leaf surface.*—Upper surface glabrous and glossy, lower surface very sparsely pubescent and satiny.

*Leaf color.*—Mature leaves upper surface; 136A, mature leaves lower surface; 137B, young leaves upper surface 137B, young leaves lower surface 137C.

*Leaf size.*—Average of 8.5 cm in length, and 7.7 cm in width.

*Leaf quantity.*—About 9 leaves per lateral branch 21 cm in length.

*Petioles.*—Average of 3.0 cm in length and 1.5 mm in diameter, 137C in color, pubescent surface.

Flower description:

*Inflorescence type.*—Flowers are solitary.

*Lastingness of flowers.*—About 1 day, self cleaning.

*Flower size.*—An average of 9 cm in depth and 5 cm in diameter.

*Flower fragrance.*—None.

*Flower shape.*—Rotate.

*Flower number.*—Average of 3 per lateral stem at one time, continuously produces throughout the summer.

*Flower aspect.*—Outward to slightly reflexed.

*Flower bud.*—Elliptic in shape, an average of 5.5 cm in length and 1.8 cm in width, color sepal portion; a blend of 144A and 144B, apex color petal portion; 23D and suffused with 39B.

*Flower attachment.*—Peduncle.

*Petal number.*—5.

*Petal shape.*—Obcordate.

*Petal color.*—Upper surface when opening and fully opened; 28D and blending into 52A in the center, a blend of 55A and 53A at the base, fine streaks of NN155B on margins, lower surface when opening and fully opened; a blend of 36A and 29C and blending into NN155B at base.

*Petal surface.*—Both surfaces smooth dull on upper portion and satiny near base.

*Petal margins.*—Very slightly crenated and slightly wavy.

*Petal apex.*—Rounded.

*Petal base.*—Slightly oblique and adnate to base of style.

*Petal size.*—Average of 5.5 cm in length and 4 cm in width.

*Sepal number.*—5.

*Sepal shape.*—Elliptic.

*Sepal margin.*—Entire.

*Sepal size.*—Average of 3 cm in length and 1 cm in width.

*Sepal aspect.*—Upright, lower 30% fused.

*Sepal surface.*—Upper (outer) surface pubescent, lower surface (inner) smooth and glossy.

*Sepal apex.*—Acute-slightly acuminate.

*Sepal base.*—Fused.

*Sepal color.*—Young and mature upper (outer) surface; blend of 144A and 144C, lower (inner) surface; 145A.

*Calyx.*—Campanulate in shape, average of 3 cm in length and 1.6 cm in diameter.

*Peduncles.*—An average of 3 cm in length and 2 mm in diameter, strong, average angle is 45° and 144A in color, finely pubescent surface.

*Pedicels.*—Not present, flowers are solitary from terminal leaf axils.

*Bracts.*—Average of 7 bracts held upright surrounding sepals, lanceolate-linear in shape, narrowly acute apex, truncate base, average of 1.5 cm in length and 3 mm in width, 139A in color on inner and outer surface, surface is slightly pubescent on inner and outer surface.

Reproductive organs:

*Gynoecium.*—1 pistil, about 4.5 cm in length, stigmas; club-shaped, an average of 5, and 14B in color, style; 3.5 cm in length and 11D from the top to midsection blending towards the base and becoming 52A in color, ovary; 9 mm in length and 8 mm in width, 11D in color and is completely covered by the base of the pistil style.

*Androecium.*—Stamens; average of 60, anthers; dorsifixed and orbicular in shape, 1 mm in diameter, and 15C in color; filament; 1 mm in length, and 11D in color, pollen; low in quantity and 15A in color.

*Fruit/seeds.*—None observed.

It is claimed:

1. A new and distinct cultivar of *Hibiscus* plant named 'Lanlampasas' as herein illustrated and described.

* * * * *